US011478277B2

(12) United States Patent
Aebi et al.

(10) Patent No.: US 11,478,277 B2
(45) Date of Patent: Oct. 25, 2022

(54) COMPRESSION NUT AND A SYSTEM FOR TREATING A BONE

(71) Applicant: DEPUY SYNTHES PRODUCTS, INC., Raynham, MA (US)

(72) Inventors: This Aebi, Grenchen (CH); Gregor Spreiter, Zurich (CH); Simon Scherrer, Zurich (CH); Henri Défossez, Neuchatel (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 189 days.

(21) Appl. No.: 16/815,762

(22) Filed: Mar. 11, 2020

(65) Prior Publication Data

US 2021/0282816 A1    Sep. 16, 2021

(51) Int. Cl.
*A61B 17/68* (2006.01)
*A61B 17/72* (2006.01)
*A61B 17/86* (2006.01)

(52) U.S. Cl.
CPC .......... *A61B 17/683* (2013.01); *A61B 17/725* (2013.01); *A61B 17/7233* (2013.01); *A61B 17/8665* (2013.01); *A61B 2017/681* (2013.01)

(58) Field of Classification Search
CPC ..... A61B 17/68; A61B 17/683; A61B 17/685; A61B 17/686; A61B 17/7233; A61B 17/7241; A61B 17/725; A61B 17/7258; A61B 17/7266; A61B 17/7275; A61B 17/8665; A61B 2017/867
USPC ...................................... 606/62–64
See application file for complete search history.

(56) References Cited

U.S. PATENT DOCUMENTS

| 6,010,505 | A | * | 1/2000 | Asche | .................. | A61B 17/683 |
| | | | | | | 606/62 |
| 6,019,761 | A | | 2/2000 | Gustilo | | |
| 2003/0040747 | A1 | | 2/2003 | Dean et al. | | |
| 2005/0240188 | A1 | | 10/2005 | Chow et al. | | |
| 2007/0014649 | A1 | | 1/2007 | James | | |
| 2010/0274296 | A1 | | 10/2010 | Appenzeller et al. | | |
| 2014/0058457 | A1 | * | 2/2014 | Appenzeller | ........ | A61B 17/864 |
| | | | | | | 606/304 |
| 2014/0155943 | A1 | | 6/2014 | Anderson | | |
| 2014/0277175 | A1 | | 9/2014 | Campbell et al. | | |
| 2015/0320450 | A1 | | 11/2015 | Mootien et al. | | |
| 2016/0135861 | A1 | | 5/2016 | Kollmer | | |

(Continued)

FOREIGN PATENT DOCUMENTS

| DE | 20 2007 017159 | 5/2008 |
| WO | 2018/021987 | 2/2018 |
| WO | 2018/021987 A1 | 2/2018 |

*Primary Examiner* — Eduardo C Robert
*Assistant Examiner* — Christina Negrellirodriguez
(74) *Attorney, Agent, or Firm* — Fay Kaplun & Marcin, LLP

(57) ABSTRACT

A compression nut for treating a bone includes a head and a body extending longitudinally from the head to a free end. The body includes a first portion including an exterior surface tapering from the head toward a second portion. An exterior threading extends along an exterior surface of both the first portion and the second portion of the body. The nut also includes a channel extending longitudinally through the body. The channel includes an interior threaded extending along an interior surface of the channel configured to threadedly engage a portion of a locking screw therein.

23 Claims, 12 Drawing Sheets

(56) References Cited

U.S. PATENT DOCUMENTS

| | | |
|---|---|---|
| 2016/0256207 A1 | 9/2016 | Zander et al. |
| 2018/0263669 A1 | 9/2018 | Peterson et al. |
| 2019/0209220 A1 | 7/2019 | Lee et al. |
| 2019/0223929 A1 | 7/2019 | Gault et al. |

* cited by examiner

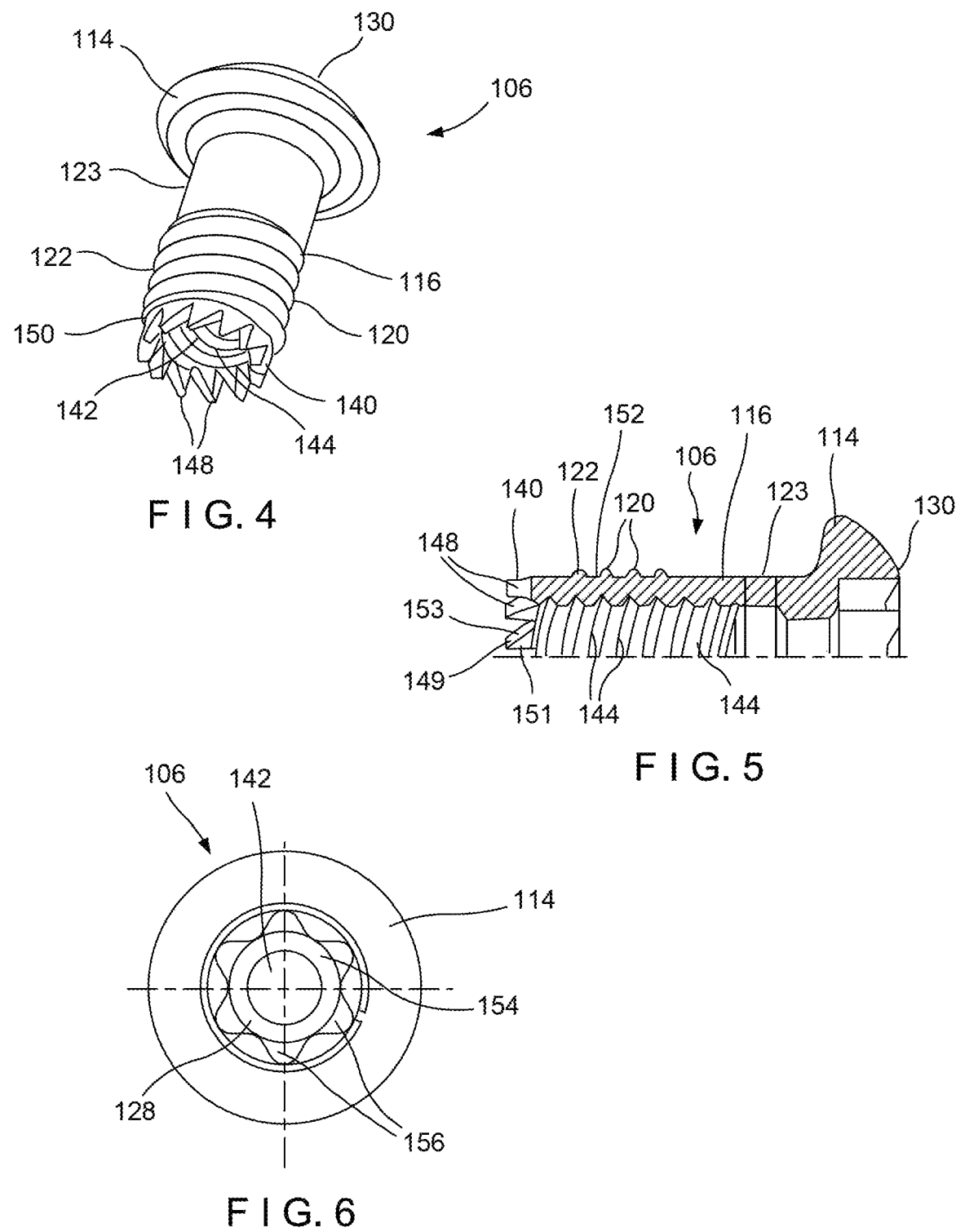

COMPRESSION NUT AND A SYSTEM FOR TREATING A BONE

FIELD

The present disclosure relates to a compression nut, a system and a method for treating a bone.

BACKGROUND

Fracture of a long bone such as, for example, a femur, may be treated using an intramedullary nail inserted through a medullary canal of the bone after the fracture has been reduced as desired. In some cases, particularly for distal condylar fractures, the bone may be treated using a retrograde nail, insertable into the medullary canal from a distal end of the bone.

Locking screws may be inserted through locking holes extending transversely through the intramedullary nail to fix the intramedullary nail to the bone and/or to provide additional stability to the bone.

SUMMARY

The present disclosure relates to a compression nut for treating a bone. The nut includes a head and a body extending longitudinally from the head to a free end. The body includes an exterior threading along an exterior surface of a threaded portion of the body separated from the head via an unthreaded portion. The nut also includes a channel extending longitudinally through the body. The channel includes an interior threaded extending along an interior surface of the channel configured to threadedly engage an end of a locking screw received therein.

In an embodiment, the free end includes cutting teeth configured for cutting bone as the compression nut is driven into a bone.

In an embodiment, a pointed tip of the cutting teeth is angled toward a rotational direction in which the compression nut is rotated to be driven into the bone.

In an embodiment, portion of the interior threading adjacent the head includes an enlarged crest for engaging a correspondingly enlarged threaded crest portion of a locking screw received therein.

In an embodiment, a portion of the interior threading proximate the free end includes an enlarged crest configured to be deformed when a threaded locking screw is received therein.

In an embodiment, the unthreaded portion of the body includes a stepped lag so that a portion of the unthreaded portion adjacent the head has a larger diameter than a remaining portion of the unthreaded portion.

In an embodiment, the head includes one or more holes extending therethrough, each of the one or more holes configured to receive an anchoring screw therein so that, when the anchoring screw is received therein, a shaft of the anchoring screw extends alongside an exterior surface of the body of the compression nut.

In an embodiment, when the head includes more than one hole, each of the holes is equidistantly spaced from an adjacent one of the holes.

In an embodiment, the compression nut further includes an anchoring screw housed within the one or more holes so that, when it is desired to anchor the compression screw to the bone, the anchoring screw may be rotated relative to the one or more holes to be driven into the bone.

In an embodiment, a portion of the body is deformed radially inward toward a longitudinal axis thereof to produce an interference with a locking screw that is threadedly received therein.

The present disclosure also relates to a system for treating a long bone. The system includes an intramedullary nail insertable through a medullary canal of a bone, the intramedullary nail extending from a proximal end to a distal end and including a locking hole extending through the intramedullary nail along an axis extending at an angle relative to a longitudinal axis of the intramedullary nail; a locking screw configured to be inserted into the bone and through the locking hole, the locking screw including a head portion and a shaft extending therefrom to a free end, the shaft including a threading extending therealong; and a first compression nut configured to be inserted into bone. The first compression nut includes a head and a body extending longitudinally from the head to a free end. The body includes an exterior threading along an exterior surface of a threaded portion of the body separated from the head via an unthreaded portion and a channel extending longitudinally therethrough. Ann interior threaded extends along an interior surface of the channel to threadedly engage a portion of the locking screw.

In an embodiment, the system further includes a second compression nut configured to be inserted into bone. The second compression nut includes a head and a body extending longitudinally from the head to a free end along with a channel extending therethrough the channel of the second compression nut including an interior threading extending therealong for threadedly receiving a portion of the shaft of the locking screw therein.

In an embodiment, a portion of the threading adjacent the head of the locking screw includes an enlarged crest and the interior threading adjacent the head of the first compression nut includes a correspondingly enlarged crest for engaging the enlarged crest of the locking screw.

In an embodiment, a portion of the interior threading proximate the free end of the first compression nut includes an enlarged crest configured to be deformed when the locking screw is threadedly received therein.

In an embodiment, the unthreaded portion of the body of the first compression nut includes a stepped lag so that a portion of the unthreaded portion adjacent the head of the first compression nut has a larger diameter than a remaining portion of the unthreaded portion.

In an embodiment, the head of the first compression nut includes one or more holes extending therethrough, each of the one or more holes configured to receive an anchoring screw therein so that, when the anchoring screw is received therein, a shaft of the anchoring screw extends alongside an exterior surface of the body of the first compression nut.

In an embodiment, the system further includes an anchoring screw housed within the one or more holes so that, when it is desired to anchor the first compression screw to the bone, the anchoring screw may be rotated relative to the one or more holes to be driven into the bone.

In an embodiment, a portion of the body of the first compression nut is deformed radially inward toward a longitudinal axis thereof resulting in an interference with the locking screw when it is threadedly received therein.

In addition, the present disclosure relates to a method for treating a bone. The method includes inserting an intramedullary nail into a medullary canal of a long bone through an insertion point at a distal end of the bone; inserting a first compression nut through the bone so that a channel of the first compression nut is substantially longitudinally aligned with a locking hole extending through a distal portion of the intramedullary nail; and driving a locking screw through the bone so that a shaft of the locking screw extends across the bone and through the locking hole, a portion of the shaft threadedly received within and engaging the first compression nut, the locking screw including a head portion from which the shaft extends to a free end.

In an embodiment, driving the locking screw through the bone includes inserting the locking screw into the bone from a side of the bone opposite the first compression nut so that the first compression nut receives and engages the free end of the shaft.

In an embodiment, driving the locking screw through the hone includes inserting the shaft through a channel of the first compression nut so that, when the locking screw is completely driven into the bone, the first compression nut engages a portion of the shaft adjacent the head portion of the locking screw.

In an embodiment, the method further includes inserting a second compression nut into the bone from a side of the bone opposite the first compression screw so that the free end of the locking screw is received within and threadedly engaged with the second compression nut.

BRIEF DESCRIPTION

FIG. 4, shows a perspective view of a compression nut according to the system of FIG. 1;

FIG. 5 shows a partial cross-sectional side view of the compression nut of FIG. 4;

FIG. 6 shows a plan view from a first end of the compression nut of FIG. 4;

DETAILED DESCRIPTION

Figure 1:
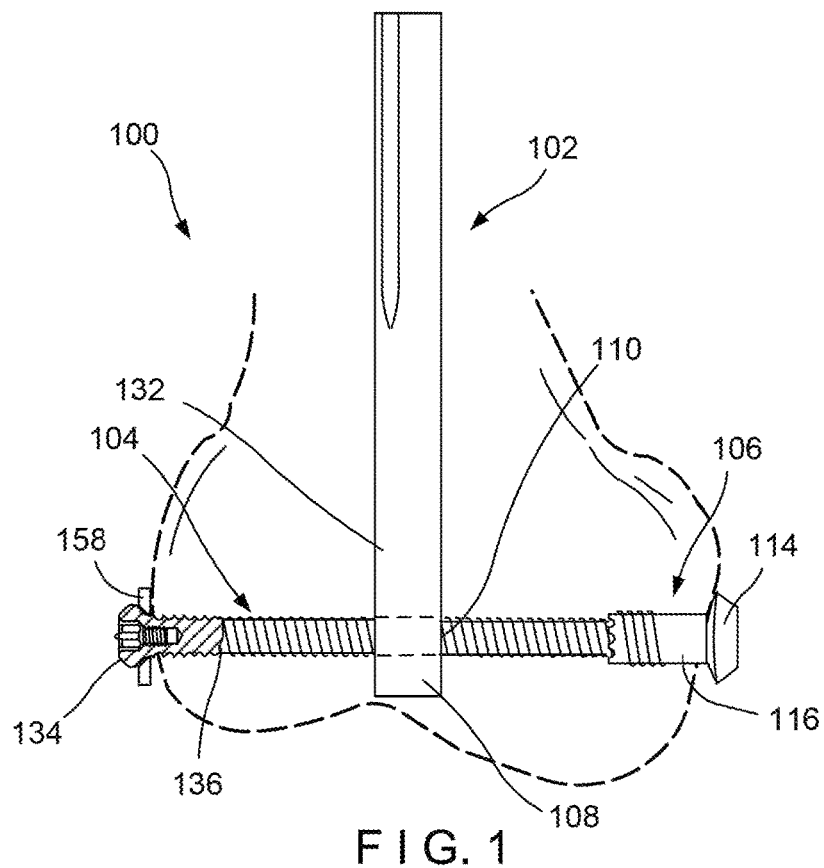
FIG. 1 shows a side view of a portion of a system according to an exemplary embodiment of the present disclosure.

The present disclosure may be understood with reference to the following description and the appended drawings, wherein like elements are referred to with the same reference numerals. The present embodiments relate to the treatment of bone and, in particular, relates to the treatment of long bones. Exemplary embodiments describe a system comprising an intramedullary nail configured to be inserted through a medullary canal of a long bone (e.g., femur) in combination with a locking screw insertable through a locking hole extending transversely through the intramedullary nail and a compression nut configured to engage a threaded end of the locking screw.

The locking screw and compression nut together act to provide additional stability, fixation and/or compression at, for example, a distal end of the bone. Exemplary embodiments describe a compression nut including a head portion and a body portion including a channel configured to threadedly receive the threaded end of the locking screw. The compression nut of this embodiment also includes an exterior threading along only a distal portion of the body portion to compress bone fragments without rotating a far fragment of the bone.

Although the exemplary embodiments specifically show and describe a retrograde femoral nail system, it will be understood by those of skill in the art that the system of the present disclosure may be used to treat any of a variety of long bones such as, for example, the humerus or tibia. Additionally, although the exemplary embodiments show and describe the locking screw and compression nut as providing stability and/compression for the distal end of the bone, it will be understood by those of skill in the art that the locking screw and compression nut may be used to provide additional stability/compression across any portion of the bone. It should be noted that the terms proximal and distal, as used herein, are intended to refer to a direction corresponding to proximal and distal ends of a bone, respectively, as will be understood by those of skill in the art.

As shown in FIGS. 1-6, a system 100 according to an exemplary embodiment of the present disclosure comprises an intramedullary nail 102 configured to be inserted through a medullary canal of a long bone (e.g., femur) along with a locking screw 104 and a compression nut 106 for securing, for example, a distal end 108 of the intramedullary nail 102 relative to the bone to provide stability and/or compression to the bone. The locking screw 104 is configured to be inserted through a locking hole 110 extending transversely through a portion of the intramedullary nail 102 from a first side of the bone. The compression nut 106 includes a head 114 and a body 116 extending therefrom, the body 116 configured to engage a free end 118 of the locking screw 104 from a second side of the bone, opposite the first side to provide additional stability, fixation and/or compression of a portion of the bone through which the locking screw 104 extends.

The body 116 includes an exterior threading 120 extending about and along a portion 122 of the body 116 separated from the head 114 so that, when the body 116 of the compression nut 106 is inserted into the bone to engage the free end 118 of the locking screw 104, compression of the bone is provided while preventing rotation of the fragmented portion of the bone. In one exemplary embodiment, the compression nut 102 may be inserted into the bone using an insertion device 124, which includes a driving end 126 sized shaped and configured to engage corresponding portions of a driving recess 128 as would be understood by those skilled in the art.

The intramedullary nail 102 extends from the distal end 108 to a proximal end (not shown). In one exemplary embodiment, the intramedullary nail 102 is retrograde femoral nail configured to be inserted through the medullary canal of a femur via an insertion point at a distal end of the bone. As would be understood by those skilled in the art, the intramedullary nail 102 of this embodiment is sized, shaped and configured to correspond to the size and shape of the medullary canal of the bone.

In one embodiment, the locking hole 110 extends transversely through a distal portion 132 of the nail 102 and is configured to receive the locking screw 104 therein to, for example, provide stability across the distal end of the femur. The locking hole 110 extends through the distal portion 132 along an axis angled with respect to a longitudinal axis of the nail 102. In one embodiment, the locking hole 110 extends through the distal portion 132 along an axis substantially perpendicular to the longitudinal axis of the of the nail 102. In another embodiment, the locking hole 110 extends through the distal portion 132 along an axis that is non-perpendicularly angled with respect to the longitudinal axis of the nail 102. Although the exemplary embodiments describe a single locking hole 110, it will be understood by those of skill in the art that the intramedullary nail 102 may include more than one locking hole 110, each of these locking holes being configured to receive a locking screw 104 therein.

Figure 2:
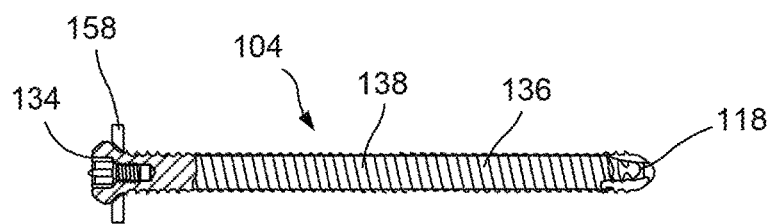
FIG. 2 shows a side view of a locking screw with a washer according to the system of FIG. 1.
Figure 3:
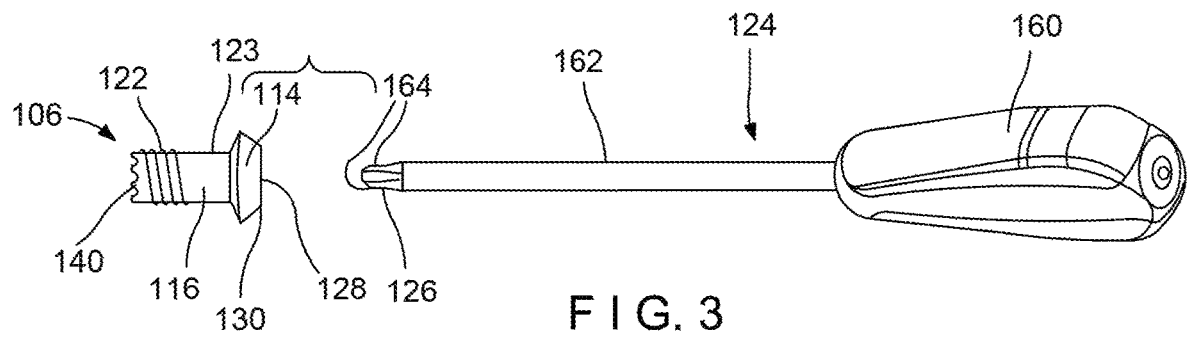
FIG. 3 shows a side view of an insertion device and compression nut according to the system of FIG. 1.

As shown in FIG. 2, the locking screw 104 according to an exemplary embodiment is a standard bone screw, as will be understood by those of skill in the art, including a head portion 134 and a shaft 136 extending therefrom to the free end 118. The shaft 136 includes a threading 138 therealong so that the locking screw 104 may be inserted into the bone and through the locking hole 110 via rotation of the locking screw 104 about a longitudinal axis thereof. As will be understood by those of skill in the art, the locking screw 104 may be driven into the bone using a driver that is, for example, engageable with a driving recess within the head portion 134. The driver and the driving recess may be correspondingly sized and shaped so that, when engaged, rotation of the driver will correspondingly rotate the locking screw 104 to drive the locking screw into the bone. The locking screw 104 is insertable into the bone and through the locking hole 110 so that, when fully inserted, the head portion 134 may abut a cortex of the bone along the first side of the bone and a length of the locking screw 104 extends substantially across a width of the bone.

As shown in FIGS. 3-6, the compression nut 106 extends from a first end 130 to a second free end 140 and includes the head 114 and a body 116 extending from the head 114 to the second end 140. The body 116 includes a channel 142 extending longitudinally thereinto from the second end 140. The channel 142 is configured to receive the free end 118 of the locking screw 104 therein and includes an interior threading 144 along an interior surface 146 thereof. The interior threading 144 corresponds to the threading 138 of the locking screw 104 so that, when rotated about the shaft 136 of the locking screw 104, the interior threading 144 of the compression nut 106 engages the threading 138 of the locking screw 104.

The free end 140 of the body 116 according to this embodiment includes a plurality of cutting teeth 148 extending about a surface 150 of the compression nut 106 which, when the compression nut 106 is being inserted into the bone faces a cortex of the bone. The cutting teeth 148 include sharp edges to facilitate cutting of the bone as the body 116 of the compression nut 106 is being inserted into the bone. In one embodiment, pointed tips 149 of the of the cutting teeth 148 are angled in a direction corresponding to a rotational direction in which the compression nut 106 will be rotated to drive the compression nut 106 into the bone. Each cutting tooth 148 is defined via a first edge 151 and a second edge 153 angled toward one another to a pointed tip 149. In one example, the first edge 151 may extend substantially parallel to a longitudinal axis of the compression nut 106 while the second edge 153 is angled relative thereto toward the pointed tip 149.

The body 116 of the compression nut 106 also includes, as described above, the exterior threading 120 extending about an exterior surface 152 along the portion 122 of the body 116 separated from the head 114 via an unthreaded portion 123. The threaded portion 122 may have an exemplary range of 1 mm to 5 mm and the unthreaded portion 123 may have an exemplary range of 0 mm to 15 mm. In one embodiment, the threaded portion 122 extends proximate the free end 140. Thus, when the compression nut 106 is driven into the bone, the exterior threading 120 engages the bone as the compression nut 106 is threaded over the locking screw 104 to provide compression to the bone while also preventing rotation of a fragmented portion of the bone along, for example, the second side of the bone. In particular, the compression nut 106 may be driven into the second side of the bone opposite the first side, so that a longitudinal axis of the compression nut 106 is in substantial alignment with the longitudinal axis of the locking screw 104 that has been inserted through the locking hole so that, as the compression nut 106 is driven into the bone, the body 116 is threaded over the free end 118 of the locking screw 104.

Similarly to the locking screw 104, the head 114 of the compression nut 106 includes the driving recess 128, which is engageable with a driver such as, for example, the insertion device 124, which drives the compression nut 106 into the bone via a rotation of the compression nut 106. In one embodiment, the driving recess 128 is open to and in communication with the channel 142. In this embodiment, each of the driving recess 128 and the channel 142 are axially aligned with a longitudinal axis of the compression nut 106. In an exemplary embodiment, the driving recess 128 includes a central portion 154 and a plurality of engaging recesses 156 extending radially therefrom. In one embodiment, each of the engaging recesses 156 may be equidistantly spaced from one another. The central portion 154 and the plurality of engaging recesses 156 may be sized, shaped and configured so that a correspondingly sized and shaped driving tip 126 of the insertion is receivable and engageable therewith so that a rotation of the insertion device 124 about a longitudinal axis thereof correspondingly rotates the compression nut 106.

In one embodiment, the insertion device 124 includes a handle portion 160 and a shaft 162 extending therefrom to the driving tip 126. As described above, the driving tip 126 is sized and shaped to be received within the driving recess 128 of the compression nut 106. In particular, the driving tip 126 includes a plurality of radially outwardly extending protrusions 164 extending from the shaft 162, each of the protrusions 164 being received in a corresponding one of the engaging recesses 156 of the driving recess 128. In one embodiment, a number of protrusions 164 corresponds to a number of a recesses 156.

According to an exemplary method, the system 100 may be used to treat fractures of long bones and, in particular, may be used to treat fractures of the distal femur. In this embodiment, the intramedullary nail 102 is inserted through a distal end of the femur so that the distal portion 132 of the intramedullary nail 102 is received within the distal end of the femur. A pilot hole may be drilled through the distal end of the bone using, for example, a drill bit, so that the pilot hole extends across the bone and through the locking hole 110 of the intramedullary nail. Once the pilot hole has been drilled, a guide wire may be inserted through the pilot hole so that ends of the guide wire extend from exterior surfaces of the bone on the first and second sides of the bone.

In one embodiment, the compression nut 106 is slid over the guide wire and inserted into the bone. In particular, the cutting teeth 148 at the free end 140 of the body 116 of the compression nut 106 cut into the bone as the compression nut 106 is rotated about a longitudinal axis thereof using, for example, the insertion device 124. The compression nut 106 is driven into the bone until the body 116 is received within the bone and the head 114 abuts the exterior of the bone at the second side of the bone. Although not shown, it will be understood by those of skill in the art that the drill bit for drilling the pilot hole and/or the guide wire for guiding the compression nut 106 may be aimed and guided into the bone and through the locking hole 110 via the use of an aiming arm or other similar device coupled to, for example, the distal end 108 of the intramedullary nail 102 as would be understood by those skilled in the art.

Upon insertion of the compression nut 106 into the bone, the guide wire may be removed from the bone and the locking screw 104 may be inserted through the pilot hole, from the first side of the bone. The locking screw 104 is driven through the pilot hole and through the locking hole 110 of the intramedullary nail 102 until the free end 118 of the shaft 136 is received within the channel 142 of the compression nut 106 and the threading 138 along the free end 118 threadedly engages the interior threading 144 extending along the channel 142 of the compression nut 106. The shaft 136 extends across the bone and the head portion 134 of the locking screw 104 abuts the cortex along the first side of the bone. Although the head portion 134 is described as abutting the bone, it will be understood by those of skill in the art that a washer 158 may be positioned between the head portion 134 and the cortex of the bone. Once the locking screw 104 and the compression nut 106 have been inserted into the bone to engage one another, a final compression may be controlled by further rotating one of the locking screw 104 and the compression nut 106.

Figure 7:
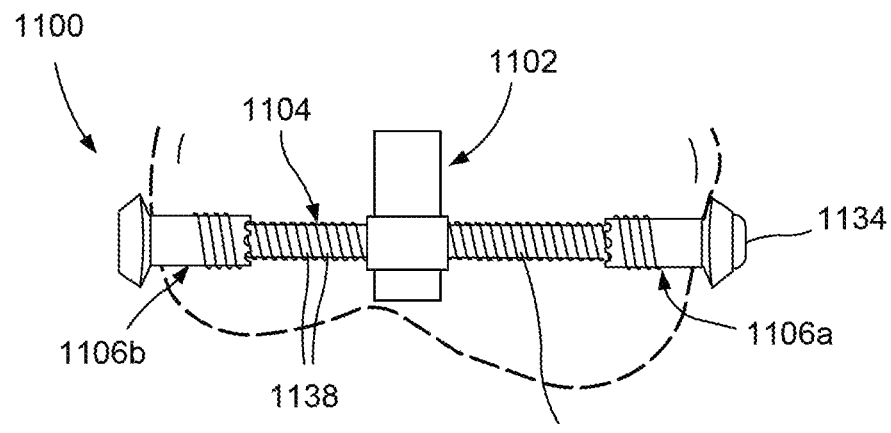
FIG. 7 shows a system according to another exemplary embodiment of the present disclosure.
Figure 8:
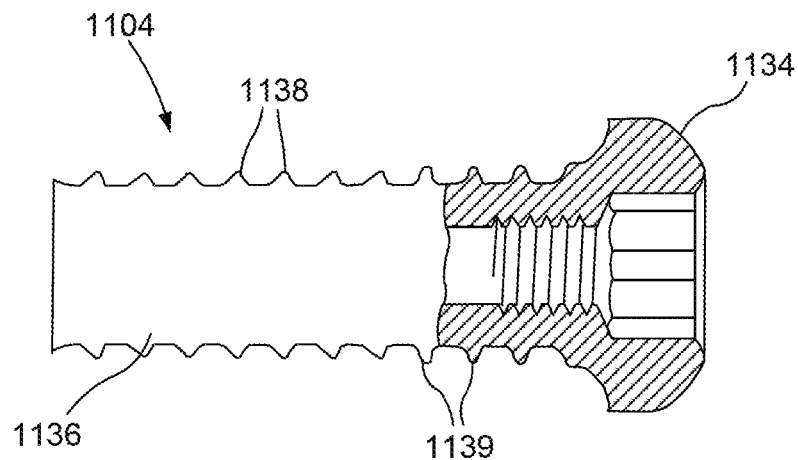
FIG. 8 shows a portion of a locking screw according to the system of FIG. 7.
Figure 9:
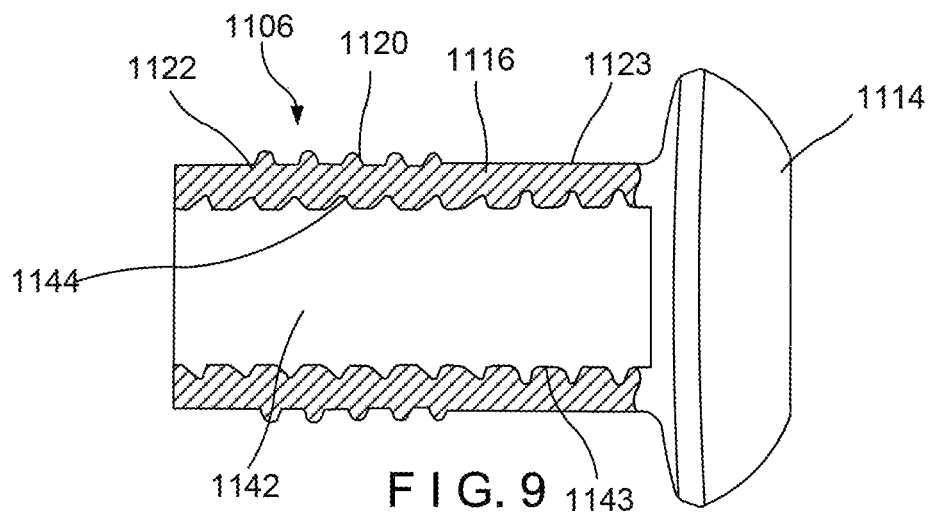
FIG. 9 shows a cross-sectional view of a compression nut according to the system of FIG. 7.

According to anther exemplary system 1100, as shown in FIGS. 7-9, a system 1100 comprises two compression nuts 1106 (1106a, 1106b) that may be used to fix both ends of a locking screw 1104 to increase nail construct stability. The locking screw 1104 may be substantially similar to the locking screw 1104, including a head portion 1134 and a shaft 1136, the shaft 1136 having a threading 1138 extending along an exterior surface thereof. In one embodiment, as shown in FIG. 8, the threading 1138 includes an enlarged crest 1139 along a portion of the shaft 1136 adjacent the head 1134 relative to a remaining portion of the shaft 1136.

Each of the two compression nuts 1106 may be substantially similar to the nut 106 of the system 100, including an exterior threading 1120 along a portion 1122 of a body 1116 separated from a head 1114 via an unthreaded portion 1123. In this embodiment, however, as shown in FIG. 9, an inner threading 1144 along a channel 1142 extending through the body 1116 of the compression nuts 1106a and 1106b matches the threading 1138 along the shaft 1136 of the locking screw 1104 to ease assembly of the first compression nut 1106a and the locking screw 1104. In particular, the portion of the inner threading 1144 along a portion 1143 of the channel 1142 adjacent the head 1114 corresponds to the enlarged thread crest 1139 of the shaft 1136.

Similarly to the exemplary method described above with respect to the system 100, when utilizing the system 1100, an intramedullary nail 1102 may be inserted into the bone, and a pilot hole drilled across the bone, through a locking hole 1110 extending transversely through a portion of the intramedullary nail 102. In this embodiment, however, the first nut 1106a is inserted through a cortex along a first side of a bone until a head portion 1114 of the first nut 1106 contacts the cortex along the first side. A free end of the locking screw 1104 is inserted into the head portion 1114 of the first nut 1106a and through a body 1116 of the nut 1106a so that a shaft 1136 of the locking screw 1104 engages a threading along an interior of the body 1116. Since the threading 1138 of the shaft 1136 matches the inner threading 1144 of the first compression nut 1106a, the locking screw 1104 may be easily moved longitudinally relative to the first nut 1106a until the free end extends beyond the body 1116 and a head portion 1134 of the locking screw 1104 abuts the head portion 1114 of the first nut 1106a. In other words, the enlarged thread crest 1139 resides within and engages the portion 1143 of the channel 1142 adjacent the head 1114 of the compression nut 1106a.

Once the locking screw 1104 has been inserted through the first nut 1106a and into the bone, as described above, the second nut 1106b may be inserted through a cortex along a second side of the bone opposite the first side to engage the free end of the locking screw 1104. Alternatively, the second compression nut 1106b may be inserted into the bone, from the second side of the bone, prior to insertion of the locking screw 1104 so that, the locking screw' is inserted through the first compression nut 1106b into the bone, until the free end of the shaft 1136 is received within and engages the body 1116 of the second compression nut 1106b. It will be understood by those of skill in the art that insertion of the compression nuts 1106a, 1106b into the bone and engagement of the free end of the shaft 1136 with the second compression nut 1106b may be substantially similar to insertion of the nut 106 as described above with respect to the system 100.

Figure 10:
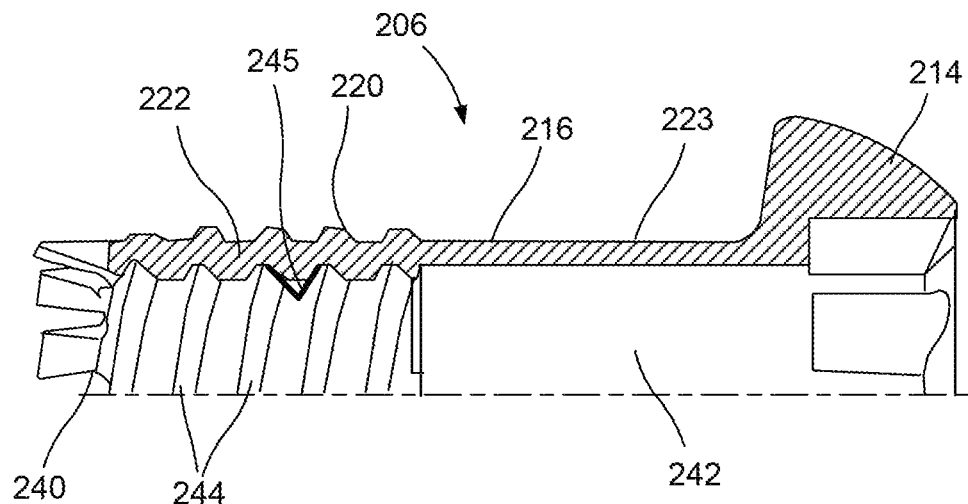
FIG. 10 shows a cross-sectional view of a compression nut according to another exemplary embodiment of the present disclosure.

As shown in FIG. 10, a compression nut 206 according to another exemplary embodiment is substantially similar to the compression nut 106 except as indicated below, and may be used in conjunction with an intramedullary nail and a locking screw, as described above with respect to the system 100. Similarly to the compression nut 106, the compression nut 206 is configured to engage a free end of a locking screw, which may be substantially similar to the locking screw 104 as described above with respect to the system 100. The compression nut 206 comprises a head 214 and a body 216 extending longitudinally therefrom to a free end 240. Similarly to the compression nut 106, the compression nut 206 includes an exterior threading 220 extending along a threaded portion 222 of the body 216 separated from the head 214 via an unthreaded portion 223 of the body 216. Similarly to the compression nut 106, the compression nut 206 also includes a channel 242 extending longitudinally thereinto from the free end 240, the channel 242 including an inner threading 244 configured to receive and engage the end of the locking screw therein.

In this embodiment, however, a portion of the inner threading 244 includes an enlarged crest 245 configured to prevent or reduce loosening of the compression nut 206 post-op, which may result from cyclical loading on the assembly (e.g., intramedullary nail, locking screw and compression nut 206). In particular, as the free end of the locking screw 104 is threadedly engaged with the channel 242 of the compression nut 206, the enlarged crest 245 deforms to lock the locking screw relative to the compression nut 206 once the locking screw and the compression nut 206 have been fully assembled. The enlarged crest 245 extends along only a portion of the threading 244 to ease an initial assembly of the locking screw with the compression nut 206. In one embodiment, the enlarged crest 245 may extend along a single turn of the threading 244. It will be understood by those of skill in the art, however, that a portion of the threading along which the enlarged crest 245 extends may be varied, as desired.

Figure 11:
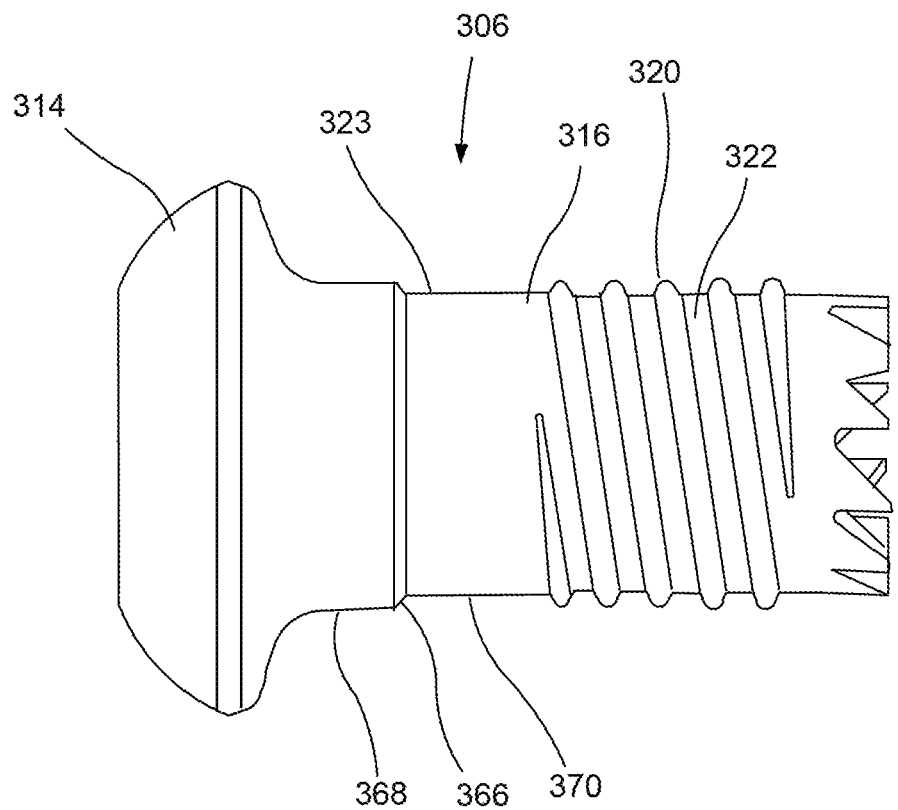
FIG. 11 shows a cross-sectional view of a compression not according to another exemplary embodiment of the present disclosure.

As shown in FIG. 11, a compression nut 306 according to another exemplary embodiment may be substantially similar to the compression nuts 106, 206, as described above except as pointed out below. Similarly, the compression nut 306 comprises a head 314 and a body 316 extending longitudinally therefrom to a free end 340. The body 316 includes an exterior threading 320 extending along a threaded portion 322, which is separated from the head 314 via an unthreaded portion 323. In this embodiment, however, the unthreaded portion 323 includes a stepped lag 366 so that a portion 368 of the unthreaded portion 323 immediately adjacent the head 314 has a larger diameter than a remaining portion 370 of the unthreaded portion 323. The smaller diameter of the remaining portion 370 permits nut compression without rotating bone fragments while the portion 368 having the larger diameter preserves stability by engaging a cortex of the bone, filling the bone area removed via the exterior threading 320 during insertion of the compression nut 306 into the bone.

Figure 12:
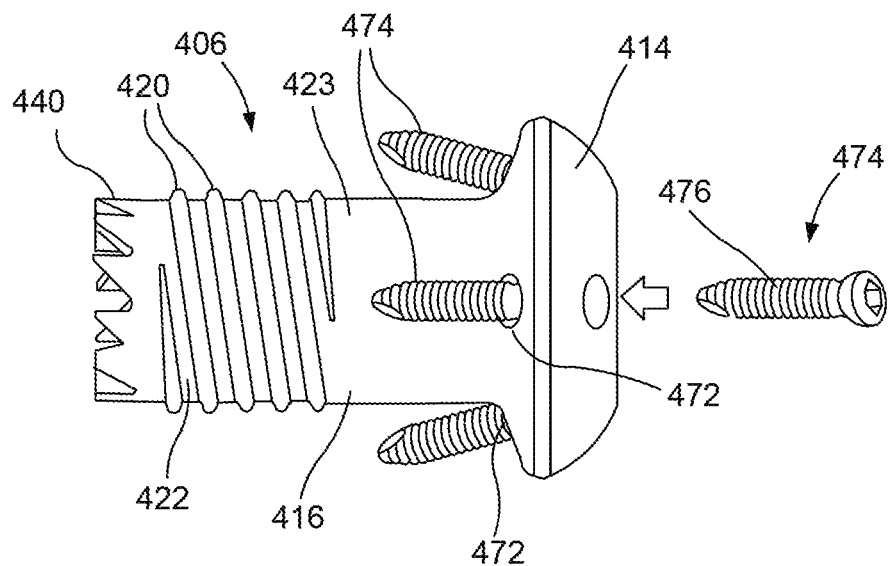
FIG. 12 shows a side view of a compression nut according to yet another exemplary embodiment of the present disclosure.

As shown in FIG. 12, a compression nut 406 according to another exemplary embodiment is substantially similar to the compression nuts 106-306 described above except as pointed out below, comprising a head 414 and a body 416 extending longitudinally therefrom to a free end 440. The body 416 includes an exterior threading 420 extending along a threaded portion 422, which is separated from the head 414 via an unthreaded portion 423. In this embodiment, however, the compression nut 406 further includes a plurality of holes 472 extending through the head 414, each hole 472 configured to receive a screw 474 therein to enhance rotational stability and increase surface area in a bone. The compression nut 406 may be particularly useful in demanding bony areas (e.g., osteoporotic bone) or demanding fracture patterns to improve load transfer.

Each of the holes 472 extends through the head 414 along an axis which, in one embodiment, is angled with respect to a longitudinal axis of the compression nut 406. The holes 472 extend through a portion of the head 414 extending about a periphery of a driving recess/channel of the compression nut 406 so that, when the screws 474 are inserted through the holes 472, shafts 476 of the screws 474 extend about a periphery of the body 416 of the compression nut 406 to extend into the bone providing enhanced anchorage of the compression nut 406 in the bone. In one embodiment, the screws 474 may be self-drilling/tapping screws. The screws 474, however, may have a variety of different lengths, diameter, pitches and/or tips. The holes 472 may have any of a variety of configurations configured to receive any of a variety of different types of screws 474. For example, the holes 472 may be non-threaded, threaded unidirectionally, or variable angle holes.

Figure 13:
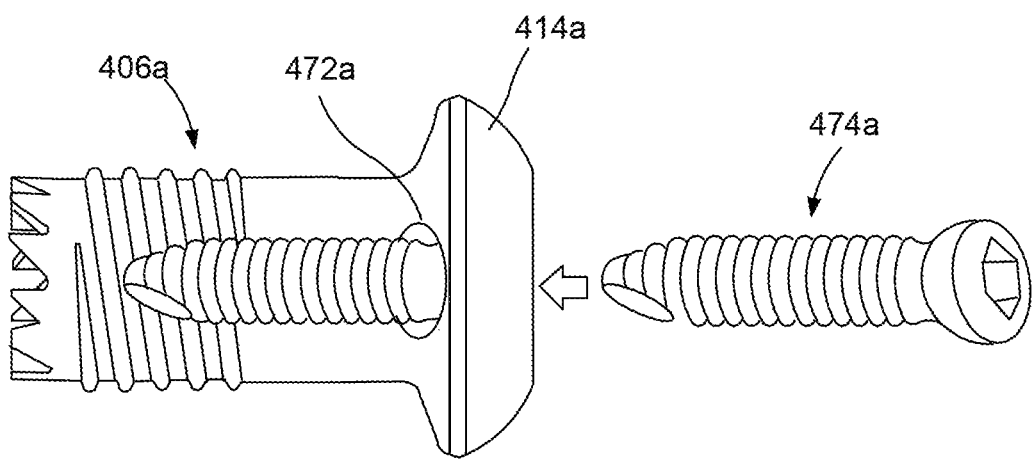
FIG. 13 shows a side view of a compression nut according to an alternate embodiment of the present disclosure.

Although the compression nut 406 is described and shown as including a plurality of holes 472, according to an alternate embodiment, as shown in FIG. 13, a compression nut 406a may include a single hole 472a extending through a head 414a of the compression nut 406a so that one larger self-tapping screw 474a may be inserted through the hole 472a to anchor the compression nut 406a to the bone.

Figure 14:
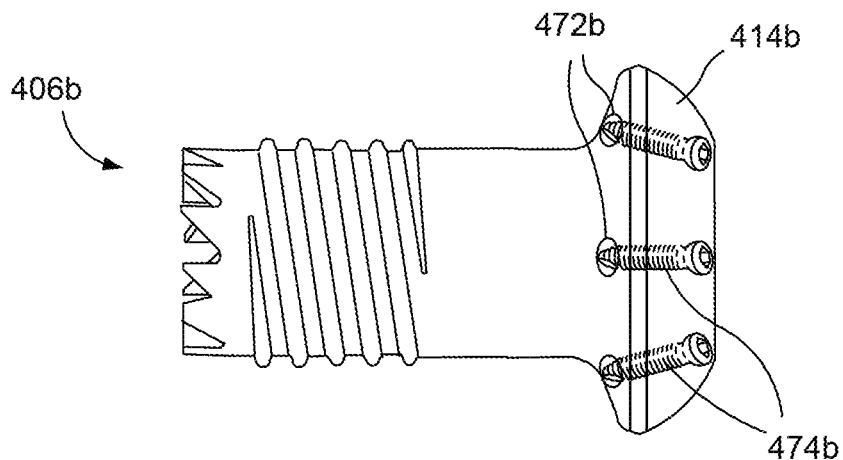
FIG. 14 shows a side view of a compression nut according to yet another alternate embodiment of the present disclosure.

According to another example, a compression nut 406b, as shown in FIG. 14, may be substantially similar to the nuts 406, 406a described above except as described below. Rather than inserting a screw through the one or more holes 472b extending through a head 414b of the compression nut 406b during a bone procedure, the compression nut 406 includes screw(s) 474b precaptured within the holes 472b, thereby saving valuable time during surgery. In particular, the screw(s) 474b are assembled/received within the holes 472b prior to insertion of the compression nut 406b into the bone. Thus, upon insertion of the compression nut 406b into the bone, a surgeon or other user may drive the one or more pre-assembled screws 474b into the bone.

Figure 15:
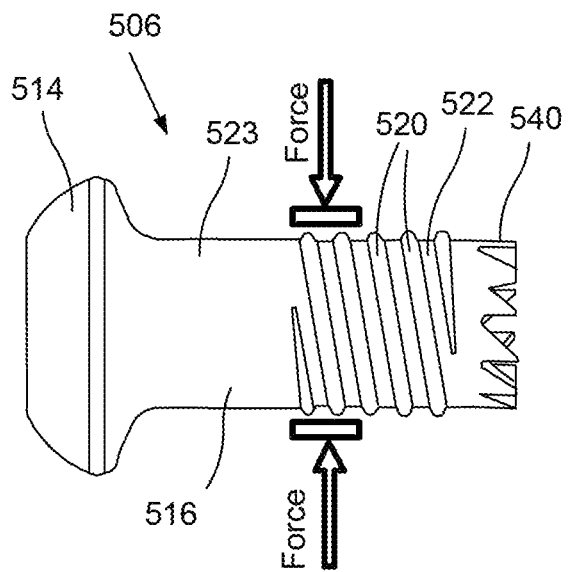
FIG. 15 shows a side view of a compression nut according to another exemplary embodiment of the present disclosure.
Figure 16:
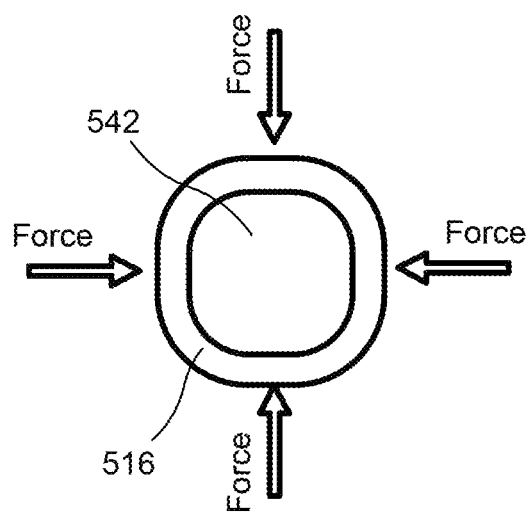
FIG. 16 shows a cross-sectional view of the compression nut according to FIG. 15.
Figure 17:
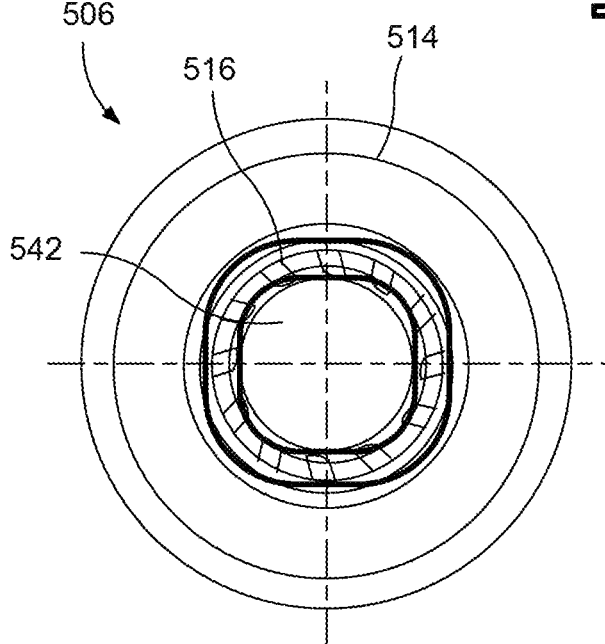
FIG. 17 shows a plan view of an end of the compression nut according to FIG. 15.
Figure 18:
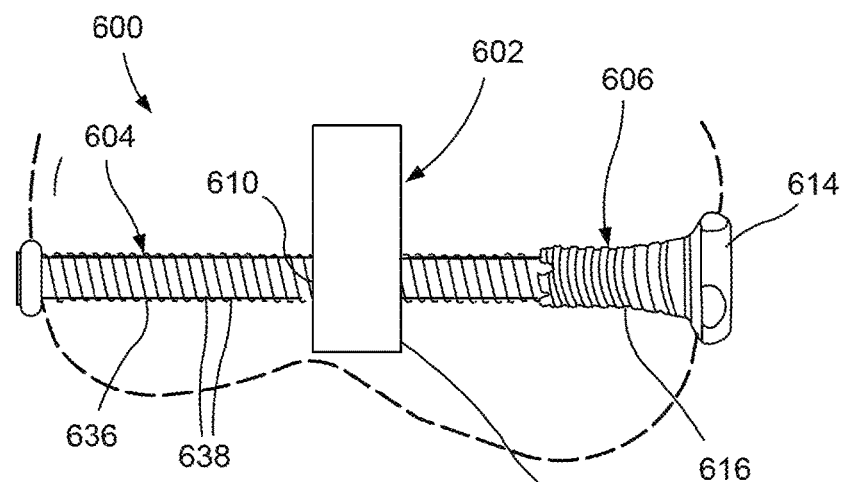
FIG. 18 shows a side view of a system according to another exemplary embodiment of the preset disclosure.
Figure 19:
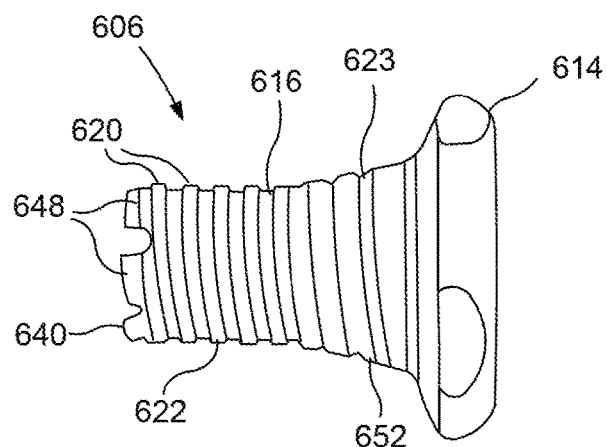
FIG. 19 shows a side view of a compression nut according to the system of FIG. 18.
Figure 20:
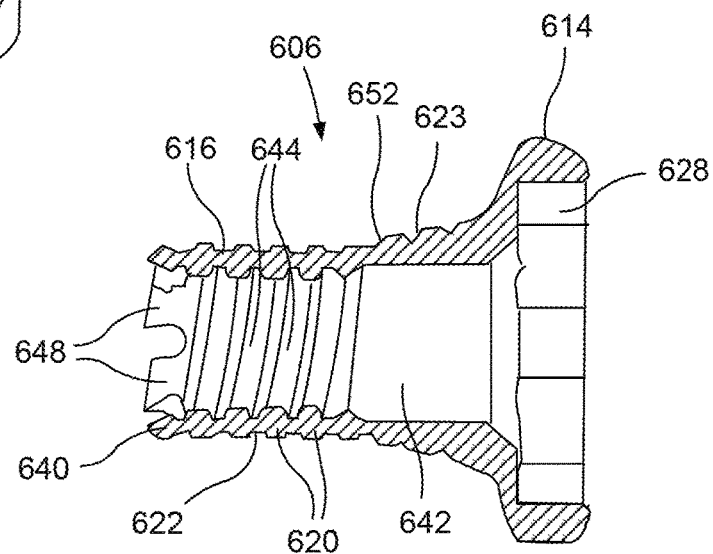
FIG. 20 shows a cross-sectional view of the compression nut of FIG. 19.

As shown in FIGS. 15-17, a compression nut 506 according to another exemplary embodiment of the present disclosure may be substantially similar to the compression nuts 106-406 described above except as described below, comprising a head 514 and a body 516 extending therefrom to a free end 540. The body 516 includes an exterior threading 520 extending along a threaded portion 522, which is separated from the head 514 via an unthreaded portion 523. The body 516 also includes a channel 542 extending therethrough, the channel 542 configured to receive a free end of a locking screw, as described above with respect to the system 100. In this embodiment, however, the body 516 is deformed to in a direction orthogonal to a longitudinal axis of the compression nut 516 to create interference with the locking screw engaged therewith, thereby reducing a loosening of the compression nut 506 during dynamic loading on the system.

In one embodiment, the body 516 is deformed during manufacturing of the compression nut 506, after both the exterior threading 520 and an interior threading along the channel 542 is manufactured. The body 516 is deformed from two or more directions pointing orthogonal to the longitudinal axis of the compression nut 506, toward the longitudinal axis. In one embodiment, as shown in FIG. 15, when the body 516 is deformed from two directions, opposing sides of the body 516 (e.g., diametrically opposed from one another) are pressed inward toward one another. In another embodiment, the body 516 is deformed in four directions (shown in FIG. 16-17), each of the directions exerting a force substantially ninety degrees relative to one another.

It will be understood by those of skill in the art, however, that deformation of the body 516 may result from forces exerted from any number of directions positioned in any of a variety of configurations relative to one another. It will also be understood by those of skill in the art that FIGS. 16-17 show an exaggerated deformation of the body 516 and that the body 516 is deformed sufficiently to result in interference with the locking screw without preventing rotation of the compression nut 506 and locking screw relative to one another and rotation of the compression nut 506 into the bone. In the exemplary embodiments mentioned above, the compression nut 506 may have an exemplary deformation of 0.1 mm to 1 mm.

As shown in FIGS. 18-22, a system 600 according to another exemplary embodiment of the present disclosure may be substantially similar to the system 100 described above. The system 600 similarly includes an intramedullary nail 602 configured to be inserted through a medullary canal of a long bone along with a locking screw 604 and a compression nut 606 for securing, for example, a distal end 608 of the intramedullary nail 602 relative to the bone to provide stability and/or compression to the bone. The locking screw 604 is configured to be inserted through a locking hole 610 extending transversely through a portion of the intramedullary nail 602 from a first side of a bone toward a second side of the bone.

The intramedullary nail 602 and the locking screw 604 are substantially similar to the intramedullary nail 602 and the locking screw 604 of the intramedullary nail 102 and locking screw 104, as described above with respect to the system 100. The compression nut 606 is also substantially similar to the compression nut 106, comprising a head 614 and a body 616 extending therefrom. In this embodiment, however, the body 616 includes a first portion 623 and a second portion 622. The first portion 623 includes an exterior surface 652 tapering from the head 624 toward the second portion 622, which has a substantially consistent cross-section along a length thereof. The first portion 623 provides a tapered transition from the head 614 along the body 616 to provide a better fit with a geometry of the bone and to prevent soft tissue irritation. The system 600 may further comprises an insertion device 624 including a driving tip 626 specifically sized, shaped and configured to engage a driving recess 628 of the compression nut 606, as will be described in further detail below.

The compression nut 606 includes the head 614 and the body 616 extending therefrom to a free end 640. As described above, the body 616 further includes the first portion 623 tapering from the head 614 toward the second portion 622. In one embodiment, the exterior surface 652 of the first portion 623 is substantially conical, while the second portion 622 is substantially cylindrical. An exterior threading 620 extends along both the first portion 623 and the second portion 622, which includes the free end 640. Similarly to the compression nut 106, the free end 640 includes cutting teeth 648 to facilitate cutting of the bone as the compression nut is being inserted therein. The compression nut 606 also includes a channel 642 extending therethrough, the channel 642 included an interior threading 644 extending therealong for engaging, for example, a threading 638 along a free end of a shaft 636 of the locking screw 604.

Figure 21:
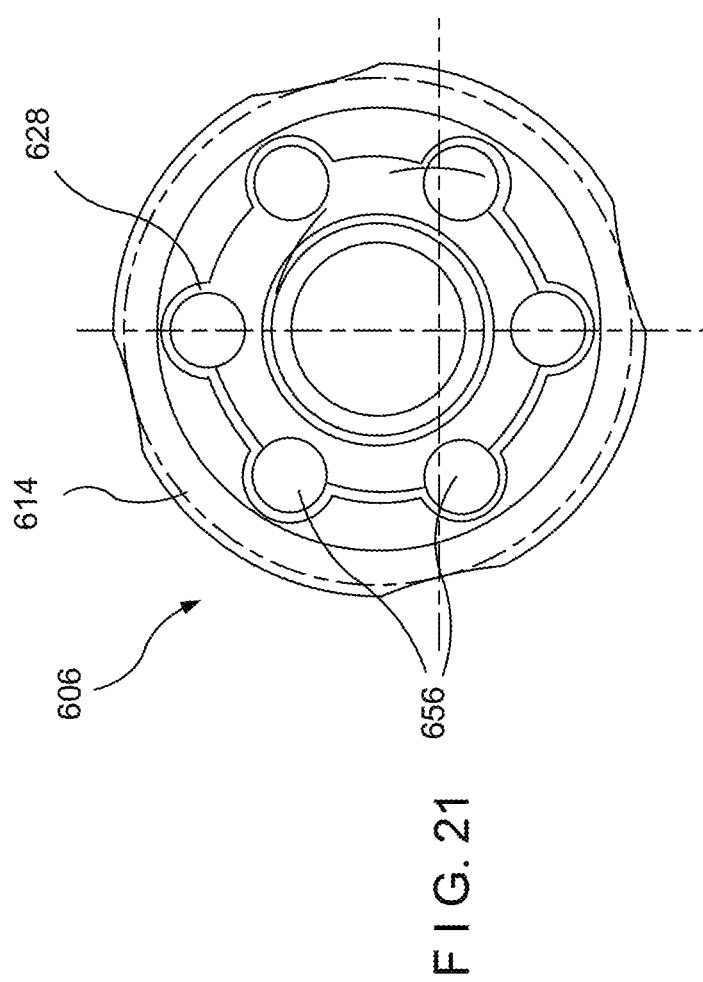
FIG. 21 shows a plan view from an end of the compression nut of FIG. 19.

As shown in FIG. 21, the head 614 of the compression nut 606 includes a driving recess 628 configured to engaging a driving tip 626 of the insertion device 624. The driving recess 628, however, is comprised of a plurality of recesses 656 extending into the head 614, each of the recesses 656 configured to receive a corresponding portion of the driving tip 626 of the insertion device 624. The recesses 656 extend into the head 614 about a periphery of the channel 642. In one embodiment, each of the recesses 656 may be equidistantly spaced from an adjacent one of the recesses 656. In one embodiment, as shown in FIG. 21, each of the recesses 656 has a substantially circular cross-section. It will be understood by those of skill in the art, however, that the recesses 656 of the driving recess 628 may be configured in any of a number of orientations and may have any of a variety of shapes and sizes so long as the driving recess is configured to receive and engage a correspondingly sized and shaped driving tip 626 of the insertion device 624.

Figure 22:
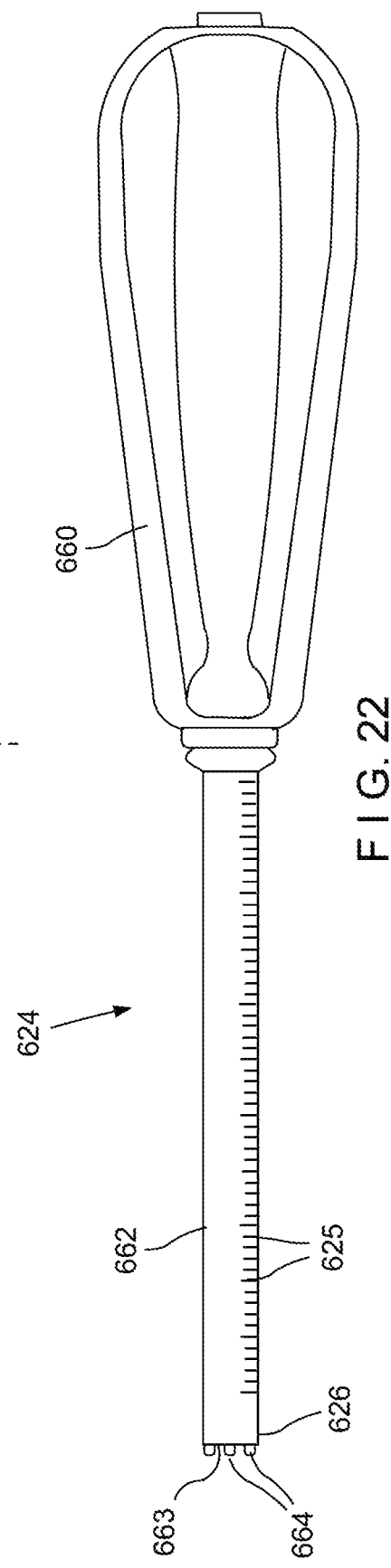
FIG. 22 shows a side view of an insertion device according to the system of FIG. 18.

The insertion device 624, as shown in FIG. 22, may be substantially similar to the insertion device 124, including a handle portion 660 and a shaft 662 extending therefrom. The shaft 662 may include a channel extending therethrough so that, in one embodiment, the shaft 662 is substantially tubular. The shaft 662 extends from the handle portion 660 to the driving tip 626, the driving tip 662 including a plurality of prongs 664 extending from an end face 663 of the shaft 662. Each of the prongs 664 extend from the shaft 662 substantially parallel to a longitudinal axis of the shaft 662 and is sized and shaped to be received within a corresponding one of the recesses 656 of the compression nut 606 so that, when the prongs 664 are received within the recesses 656, a rotational force exerted on the insertion device 624 will correspondingly rotate the compression nut 606 to drive the compression nut 606 into the bone.

It will be understood by those of skill in the art that insertion of the various components of the system 600 into the bone requires a large number of x-rays to control a progression of the locking screw 604 and/or compression nut 606 into the bone. In one embodiment, the shaft 662 of the insertion member 624 includes markings 625 along a length of the shaft 662 so that a position of the markings 625 relative to a portion of, for example, an aiming arm through which the shaft 662 is passed to insert the compression nut 606 into the bone, indicates to a surgeon or other user a progression of the compression nut 606 into the bone.

Figure 23:
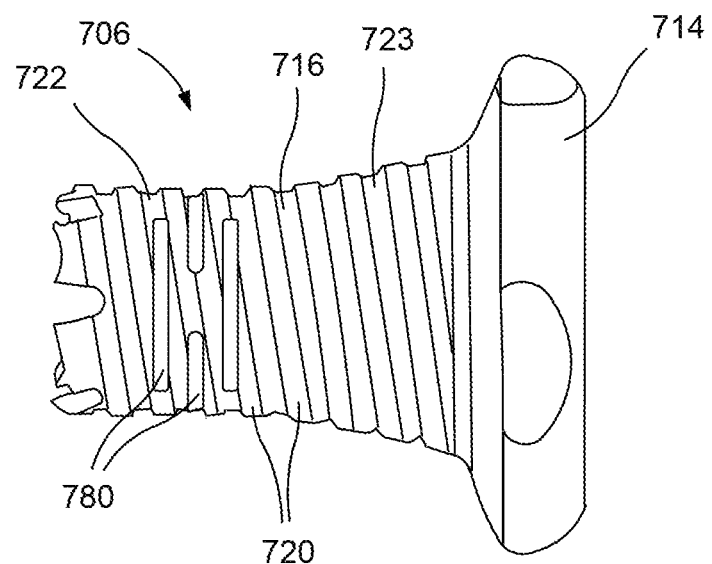
FIG. 23 shows a side view of a compression nut according to another exemplary embodiment of the present disclosure.
Figure 24:
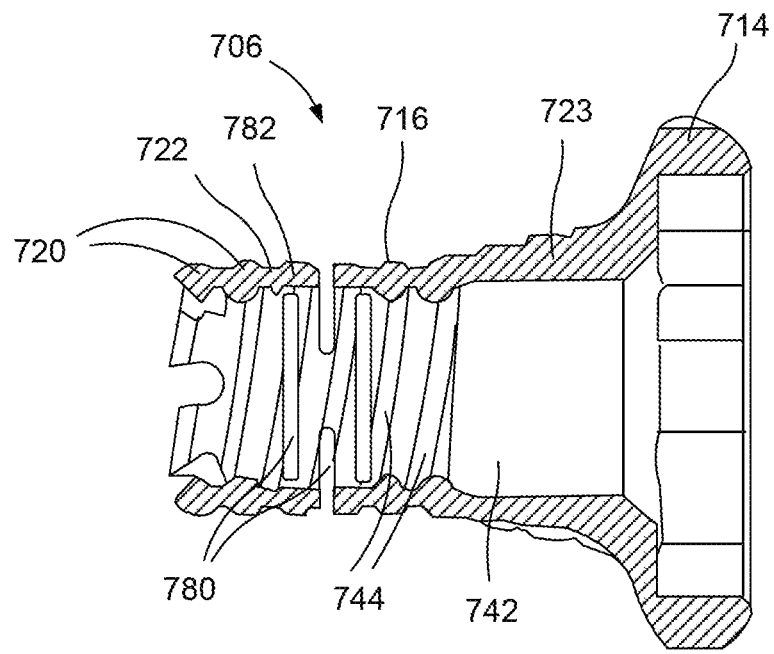
FIG. 24 shows a cross-sectional view of the compression nut of FIG. 23.

As shown in FIG. 23-24, a compression nut 706 according to another exemplary embodiment of the present disclosure may be substantially similar to the compression nut 606, as described above with respect to the system 600, and may be used in substantially the same manner in conjunction with the intramedullary nail 602 and the locking screw 604. Similarly to the compression nut 606, the compression nut 706 includes a head 714 and a body 716 extending therefrom, the body 716 including a first transitional tapered portion 723 extending from the head 714 to a second portion 722. An exterior threading 720 extends along both the first and second portions 723, 722. The compression nut 706 also includes a channel 742 extending therethrough, the channel 742 including an interior threading 744 extending therealong so that, when the compression nut 706 is threadable over, for example, a free end of the locking screw 604.

To enhance an engagement between the locking screw and the compression nut 706, however, the body 716 includes a plurality of slots 780 extending through a wall 782 thereof, the wall defined via an interior surface of the channel 742 an exterior surface of the body 716 so that an interior of the channel 742 is open to an exterior of the compression nut 706 via the slots 780. The slots 780 permit a deformation of the body 716 relative to the locking screw to provide a controlled interference therebetween. In one embodiment, the slots 780 extend through the second portion 722 of the body 716.

In one embodiment, the slots 780 may extend transversely through the wall 782 of the body 716 to permit a deformation of the body 716, which creates a spring-loaded mismatch between the interior threading 744 of the compression nut 706 and threads of the locking screw received therein. In this embodiment, the slots 780 extend substantially perpendicular relative to a longitudinal axis of the compression nut 706, extending about a portion of a circumference of the body 716. In an exemplary embodiment, the portion of the circumference of the body 716 may be from 90° to 170°. Moreover, the spring-loaded mismatch may be created by the compression nut 706 being compressed or stretched during manufacturing.

The plurality of slots 780 extending about a portion of a circumference of the body 716 and along a portion of a length of the body 716. In one embodiment, adjacent ones of the plurality of slots 780 may be offset relative to one another along a length of the body 716. The transverse configuration of the slots 780 permit a longitudinal expansion or compression of the body 716 along the longitudinal axis of the compression nut 706 as well as a bending relative to the longitudinal axis of the compression nut 706 or a twisting of the body 716 about the longitudinal axis of the compression nut 706, which results in a mis-match of thread pitch and/or direction between the exterior threading of the locking screw and the interior threading 744 of the compression nut 706. This interference between the compression nut 706 and the locking screw retains the compression nut 706 over the locking screw 704 to prevent/reduce a loosening of the compression nut 706 post-op.

Figure 25:
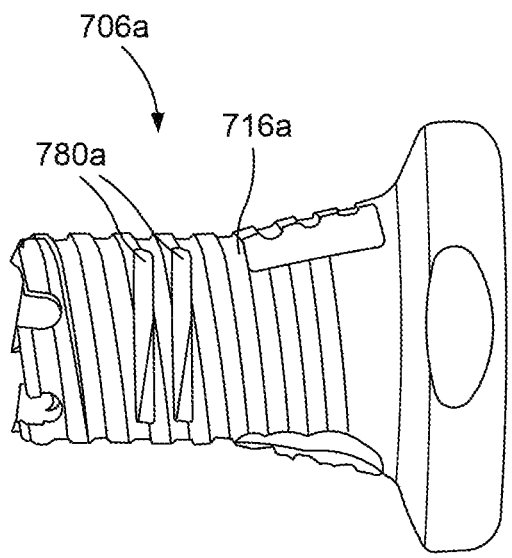
FIG. 25 shows a side view of a compression nut according to an alternate embodiment.
Figure 26:
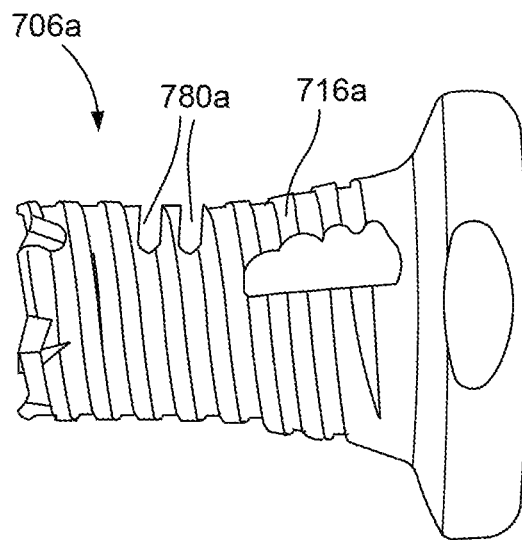
FIG. 26 shows another side view of the compression nut of FIG. 25, rotated approximately 90 degrees about a longitudinal axis thereof.

In an alternate embodiment, as shown in FIGS. 25-26, a compression nut 706a may be substantially similar to the compression nut 706, as described above, including a plurality of transverse slots 780a extending through a body 716a thereof. Rather than being offset from one another along a length of the body 716a, however, adjacent ones of the slots 780a may be substantially aligned along the length of the body 716a. Adjacent ones of the slots 780a may or may not extend about a corresponding portion of a circumference of the body 716a ranging between approximately 90° and 170°.

Figure 27:
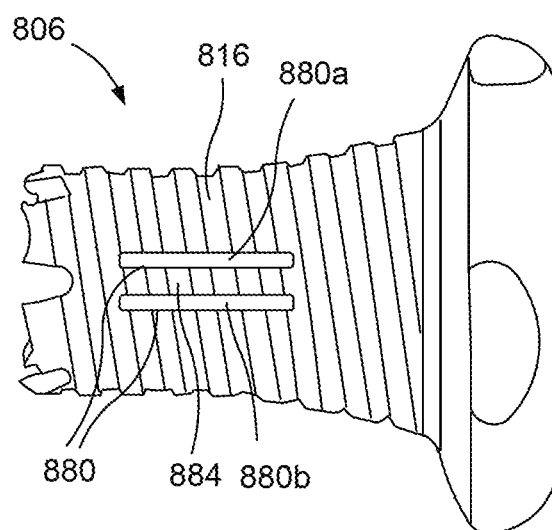
FIG. 27 shows a side view of a compression nut according to another exemplary embodiment of the present disclosure.
Figure 28:
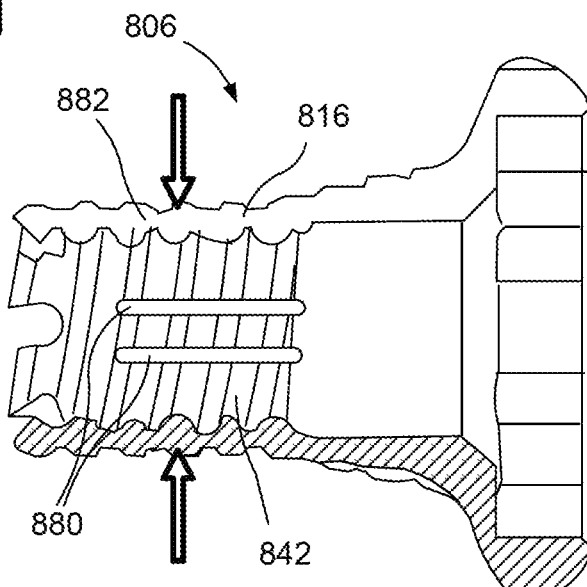
FIG. 28 shows a cross-sectional view of the compression nut of FIG. 27.
Figure 29:
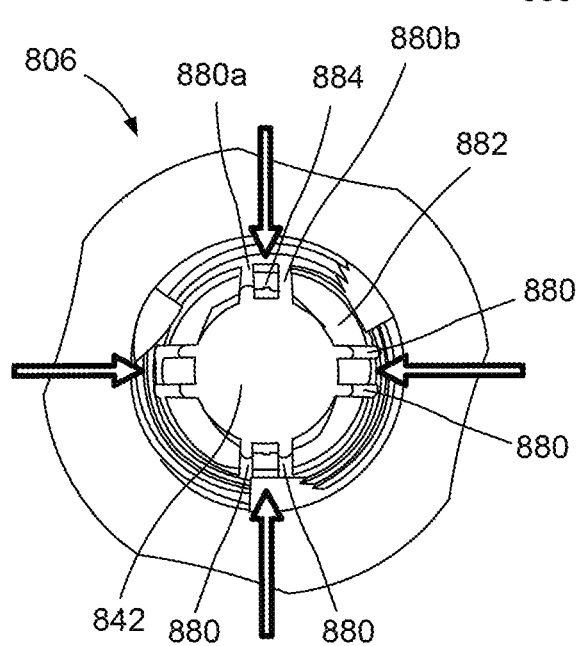
FIG. 29 shows a plan view from an end of the compression nut of FIG. 27.

In another embodiment, as shown in FIGS. 27-29, a compression nut 806 may be substantially similar to the compression nuts 706, 706a described above. Rather than transverse slots, however, the compression nut 806 includes a body 816 having slots 880 extending longitudinally through a wall 882 of the body 816. Each of the slots 880 extend along a portion of a length of the body 816 substantially parallel to a longitudinal axis of the compression nut 806. In one embodiment, slots 880 are arranged in pairs and a portion 884 of the body 816 extending between a first slot 880a and a second slot 880b of each pair of slots 880 is deformed radially inward toward the longitudinal axis of the compression nut 806 to create a desired interference between the compression nut 806 and a locking screw received within a channel 842 thereof. A distance between the first slot 880a and the second slot 880b of each pair of slots 880 may be 0.3 mm to 3 mm.

In one embodiment, the compression nut 806 includes four pairs of slots 880 to define four deformed portions 884. Each of the pairs of slots 880 may be equidistantly spaced from an adjacent one of the pairs of slots 880. It will be understood by those of skill in the art, however, that the compression nut 806 may include any number of pairs of slots 880 to define any number of deformed portions 884 having any of a variety of configurations. In the above described embodiments, the portion 884 between the first slot 880a and the second slot 880b is deformed during manufacturing.

Figure 30:
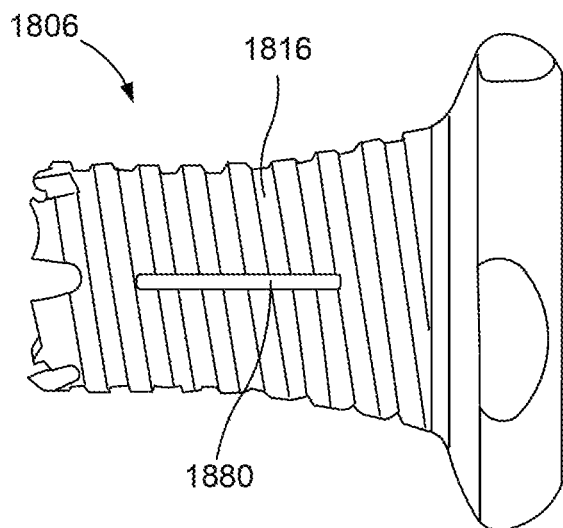
FIG. 30 shows a side view of a compression nut according to yet another exemplary embodiment of the present disclosure.
Figure 31:
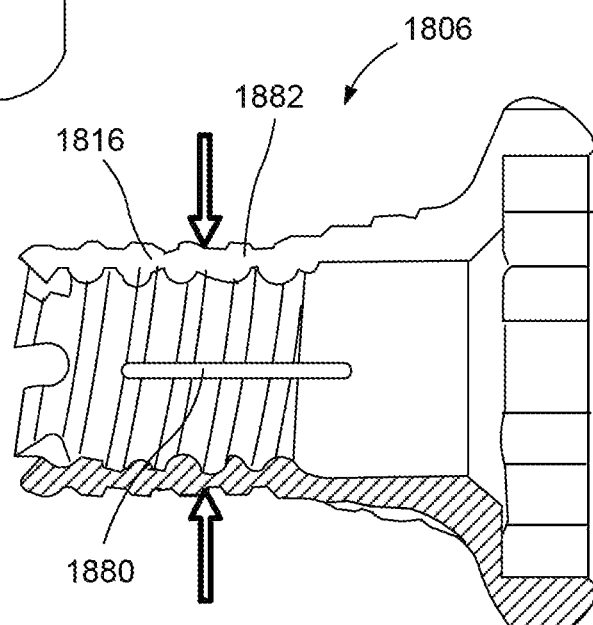
FIG. 31 shows a cross-sectional view of the compression nut of FIG. 30.
Figure 32:
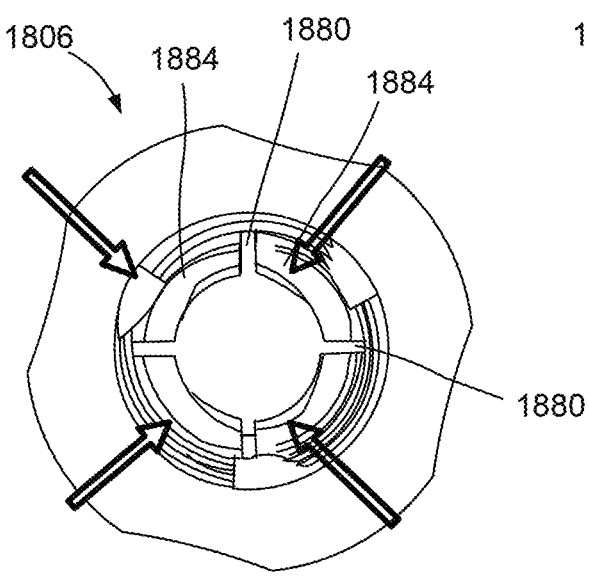
FIG. 32 shows a plan view from an end of the compression nut of FIG. 30.

FIGS. 30-32 show another embodiment of a compression nut 1806 including longitudinal slots 1880 extending through a wall 1882 of a body 1816 of the compression nut 1806. The longitudinally extending slots 1880, however, are not arranged in pairs. Rather, a portion 1884 of the body between adjacent ones of the slots 1880 is deformed radially inward toward a longitudinal axis of the compression nut 1806 so that a larger portion of the body 1816 is deformed relative to the compression nut 1806. In one embodiment, the compression nut 1806 includes four each of the longitudinal slots 1880 is equidistantly spaced from an adjacent one of the slots 1880. It will be understood by those of skill in the art, however, that the slots 1880 may be arranged in any of a number of configurations about and along the body 1816 to define deformed portions 1884.

Although the above embodiments show and describe the compression nut 706 (706a and 806, 1806) as including either transverse or longitudinal slots 780, it will be understood by those of skill in the art that the slots 780 may have any of a variety of size, shapes and configurations so long as the slots 780 are configured to permit a deformation of a body 716 of the compression nut 706, which results in an interference between the compression nut 706 and a locking screw threadedly received therewithin. For example, in another embodiment, a compression nut may include a slot extending helically about a body a portion of the body, through a wall thereof.

It will be understood by those of skill in the art that modifications and variations may be made in the structure and methodology of the present embodiment, without departing from the spirit or the scope of the embodiments. Thus, it is intended that the present embodiments cover the modifications and variations of these embodiments provided that the come within the scope of the appended claims and their equivalents.

What is claimed is:

1. A compression nut for treating a bone, comprising:
   a head and a body extending longitudinally from the head to a free end, the body including a first portion including an exterior surface tapering from the head toward a second portion, the second portion having a substantially consistent cross-section along a length thereof, an exterior threading extending along an exterior surface of the first portion and an exterior surface of the second portion of the body; and
   a channel extending longitudinally through the body and including an interior threading extending along an interior surface of the channel configured to threadedly engage a portion of a locking screw therein.

2. The compression nut of claim 1, wherein the free end includes cutting teeth configured for cutting bone as the compression nut is driven into a bone.

3. The compression nut of claim 1, wherein the first portion of the body is substantially conical and the second portion of the body is substantially cylindrical.

4. The compression nut of claim 1, further comprising a plurality of slots extending through a wall of the body, the wall defined via the interior surface of the channel and the exterior surface of the body so that the channel is open to an exterior of the compression nut via the slots.

5. The compression nut of claim 4, wherein the plurality of slots extends through the second portion of the body.

6. The compression nut of claim 4, wherein each of the plurality of slots extend transverse relative to a longitudinal axis of the compression nut so that each of the plurality of slots extend about a portion of a circumference of the body.

7. The compression nut of claim 6, wherein each of the plurality of slots are one of offset from one another and aligned relative to one another along a length of the body.

8. The compression nut of claim 4, wherein each of the plurality of slots extends longitudinally along a portion of a length of the body.

9. The compression nut of claim 8, wherein the plurality of slots are arranged in pairs so that a longitudinal portion of the body extending between a first slot and a second slot of each of the pairs is deformed radially inward toward a longitudinal axis of the compression nut.

10. The compression nut of claim 8, wherein the plurality of slots is equidistantly spaced from one another about a circumference of the body.

11. The compression nut of claim 8, wherein a portion of the body extending between adjacent one of the plurality of slots is deformed radially inward toward a longitudinal axis of the compression nut.

12. The compression nut of claim 1, wherein a diameter of the first portion is a maximum at a proximal end thereof adjacent to the head and tapers to a minimum diameter at a distal end thereof adjacent to the proximal end of the second portion.

13. The compression nut of claim 12, wherein the first portion is substantially conical and the second portion is substantially cylindrical.

14. A system for treating a long bone, comprising:
an intramedullary nail insertable through a medullary canal of a bone, the intramedullary nail extending from a proximal end to a distal end and including a locking hole extending through the intramedullary nail along an axis extending at an angle relative to a longitudinal axis of the intramedullary nail;
a locking screw configured to be inserted into the bone and through the locking hole, the locking screw including a head portion and a shaft extending therefrom to a free end, the shaft including a threading extending therealong; and
a compression nut including a head and a body extending longitudinally from the head to a free end, the body including a first portion including an exterior surface tapering from the head toward a second portion the second portion having a substantially consistent cross-section along a length thereof, an exterior threading extending along the exterior surface of both the first portion and the second portion of the body, a channel extending longitudinally through the compression nut and including an interior threading extending along a portion of an interior surface of the channel to threadedly engage a portion of the locking screw therein.

15. The system of claim 14, further comprising an insertion device including a handle member and a shaft extending therefrom to an end including a driving tip.

16. The system of claim 15, wherein the driving tip includes a plurality of prongs extending longitudinally from an end face of the shaft.

17. The system of claim 16, wherein the compression nut includes a driving recess extending into the head of the compression nut, the driving recess comprised of a plurality of recesses extending about a periphery of the channel, each of the recesses sized, shaped and configured to receive a corresponding one of the prongs therein.

18. The system of claim 17, wherein each of the plurality of recesses has a circular cross-section.

19. The system of claim 14, wherein the compression nut includes a plurality of slots extending through a wall of the body so that the channel is open to an exterior of the compression nut via the slots.

20. The system of claim 19, wherein each of the plurality of slots extend transverse relative to a longitudinal axis of the compression nut so that each of the plurality of slots extend about a portion of a circumference of the body to permit one of an expansion and compression along a longitudinal axis of the compression nut, a bending relative to the longitudinal axis and twisting about the longitudinal axis.

21. The system of claim 19, wherein each of the plurality of slots of the compression nut extend longitudinally along a portion of a length of the body.

22. The system of claim 21, wherein the plurality of slots is arranged in pairs so that a longitudinal portion of the body extending between a first slot and a second slot of each of the pairs is deformed radially inward toward a longitudinal axis of the compression nut.

23. The system of claim 19, wherein a portion of the body extending between adjacent one of the plurality of slots is deformed radially inward toward a longitudinal axis of the compression nut.

* * * * *